United States Patent [19]

Boden et al.

[11] Patent Number: 4,481,372

[45] Date of Patent: Nov. 6, 1984

[54] PROCESS FOR PREPARING ALLYL ALPHA AND BETA IONONES AND INTERMEDIATES THEREFOR

[75] Inventors: Richard M. Boden, Ocean; Steven D. Temes, Hazlet; Theodore J. Tyszkiewicz, Sayreville, all of N.J.

[73] Assignee: International Flavors & Fragrances Inc., New York, N.Y.

[21] Appl. No.: 430,941

[22] Filed: Sep. 30, 1982

[51] Int. Cl.$^3$ .................... C07C 49/21; C07C 49/543
[52] U.S. Cl. .................................. 568/378; 568/346; 568/347; 568/377; 568/328
[58] Field of Search ............... 568/378, 412, 413, 376, 568/377, 346, 347, 348; 560/126; 562/508

[56] References Cited

U.S. PATENT DOCUMENTS

| | | | |
|---|---|---|---|
| 3,030,416 | 4/1962 | Mikusch-Buchberg | 568/412 |
| 3,679,754 | 7/1972 | Beereboom | 568/348 |
| 3,923,896 | 12/1975 | Schulte-Elte | 568/377 |
| 4,157,350 | 1/1979 | Wilson et al. | 568/348 |
| 4,157,351 | 1/1979 | Mookherjee et al. | 568/348 |
| 4,272,412 | 6/1981 | Willis et al. | 568/376 |
| 4,334,098 | 6/1982 | Mookherjee | 568/347 |

FOREIGN PATENT DOCUMENTS 743138  9/1966  Canada .................... 568/412

OTHER PUBLICATIONS

White, "Journal of American Chemical Society", vol. 100, #19, Sep. 19, 1978, pp. 6296–6297.

Primary Examiner—Werren B. Lone

Attorney, Agent, or Firm—Arthur L. Liberman

[57] ABSTRACT

Described is a novel process for preparing allyl alpha and beta ionones defined according to the structure:

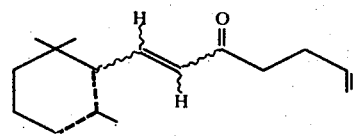

wherein one of the dashed lines represents a carbon-carbon double bond and the other of the dashed lines represents a carbon-carbon single bond; and wherein the wavy lines represent the cis or trans juxtaposition of the acyl and cyclohexenyl rings about the carbon-carbon double bond which is alpha to the acyl moiety, and intermediates used in said process defined according to the structure:

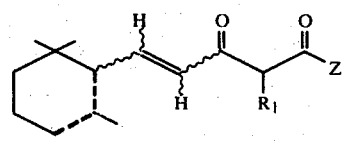

wherein the wavy lines and dashed lines are defined supra and wherein $R_1$ represents hydrogen or allyl and Z represents methyl or $OR_2$ and wherein $R_2$ represents methyl or ethyl.

8 Claims, 6 Drawing Figures

NMR SPECTRUM FOR PRODUCT A OF EXAMPLE I.

NMR SPECTRUM FOR PRODUCT B OF EXAMPLE I.

IR SPECTRUM FOR PRODUCT B OF EXAMPLE I.

GLC PROFILE FOR PRODUCT C FOR EXAMPLE I.
CRUDE

GLC PROFILE FOR PRODUCT C OF EXAMPLE I.

GLC PROFILE FOR BULKED FRACTIONS 17-21 FROM PRODUCT C OF EXAMPLE I.

PROCESS FOR PREPARING ALLYL ALPHA AND BETA IONONES AND INTERMEDIATES THEREFOR

BACKGROUND OF THE INVENTION

Allyl alpha and beta ionones are known for their uses in augmenting or enhancing the organoleptic properties of consumable materials such as foodstuffs, chewing gums, medicinal products, perfumes, perfume compositions, colognes and perfumed articles. Thus, Arctander "Perfume and Flavor Chemicals (Aroma Chemicals)", Volume I, 1969, at Monograph 86 indicates that allyl ionone ("alpha allyl ionone") having the structure:

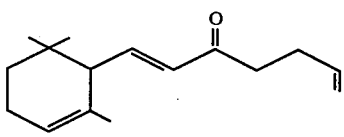

has an oily-sweet, slightly flowery but also fruity, woody and bark-like, green odor of considerable tenacity. Arctander further states that this compound is "useful in perfume compositions as a modifier for ionones and methyl ionones, in modern-aldehydic creations, in perfumes with fruity-aldehydic topnotes, in combination with vetiver or woody-floral perfume materials, etc." Arctander further states that the compound is "used in flavors—in traces—for imitation raspberry and pineapple". Arctander further states that this compound is produced from citral by condensation with allyl acetone, followed by cyclization.

There is a need to produce such allyl alpha and beta ionones in an inexpensive manner and in high purity whereby they can be more readily used in augmenting or enhancing the organoleptic properties of consumable materials.

Our invention fulfills this need by the creation of a synthesis of such allyl alpha and beta ionones inexpensively and directed towards the creation of specific derivatives.

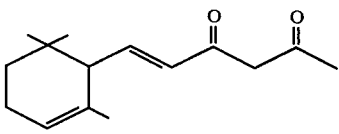

and 15% of the isomer having the structure:

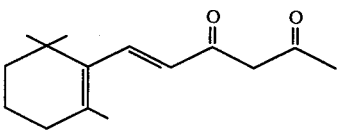

(Solvent: CFCl₃; Field strength: 100 MHz).

Figure 2:
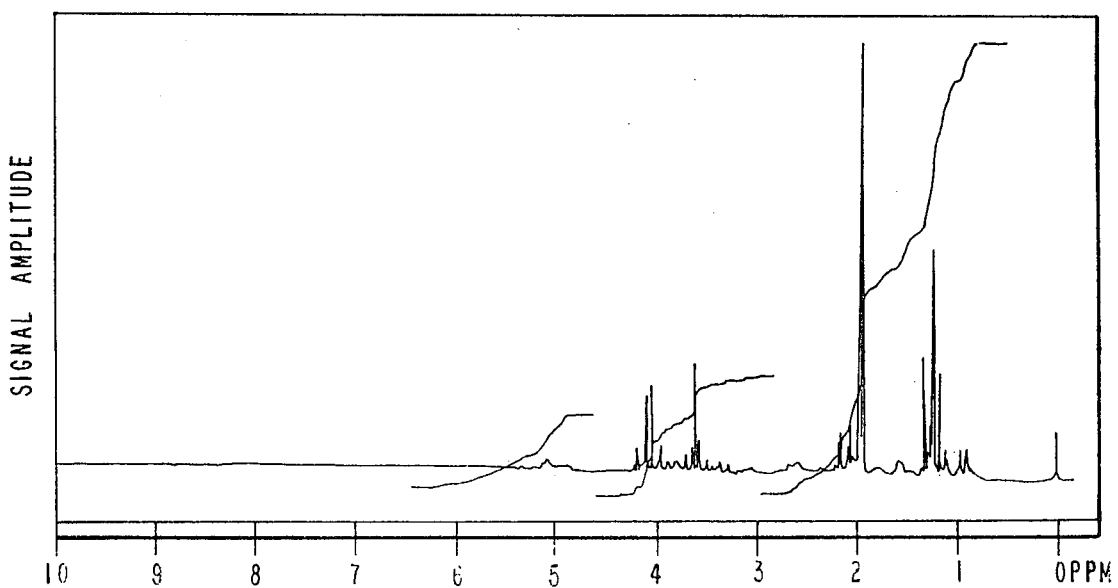

FIG. 2 is the NMR spectrum for product "B" produced according to Example I which product contains the isomer having the structures:

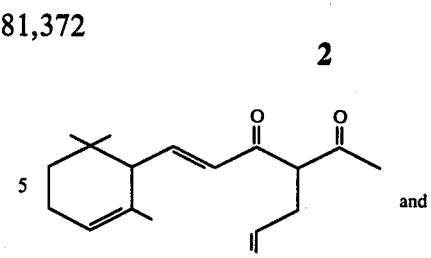

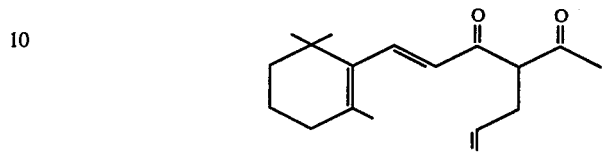

(Solvent: CFCl₃; Field strength: 100 MHz).

Figure 3:
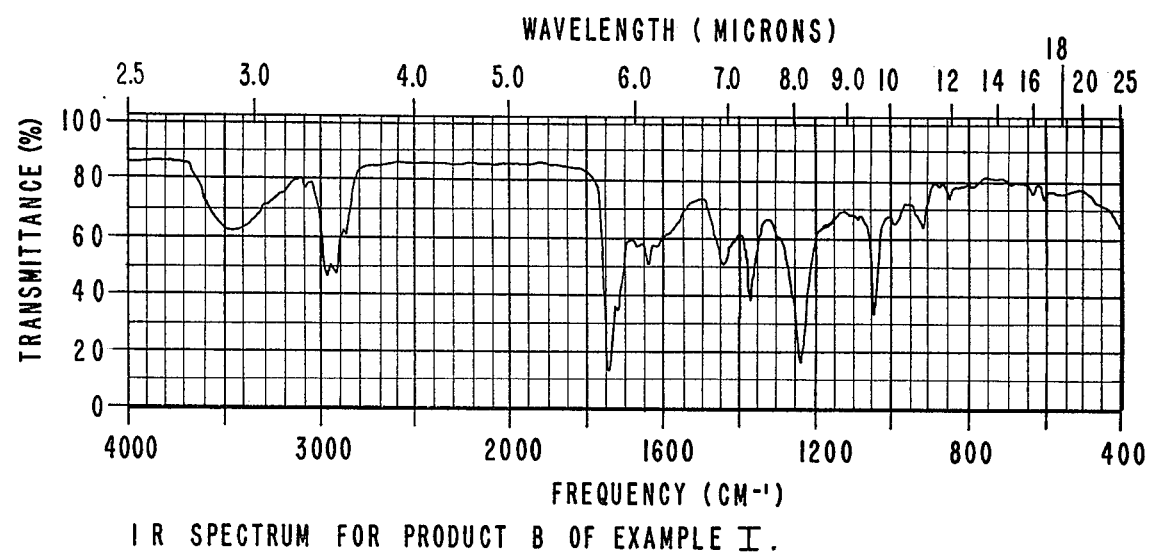

FIG. 3 is the infra-red spectrum for product "B" produced according to Example I containing the compounds having the structures:

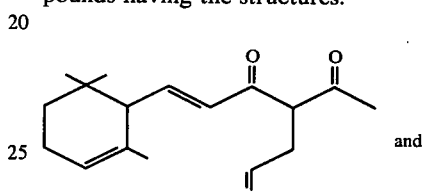

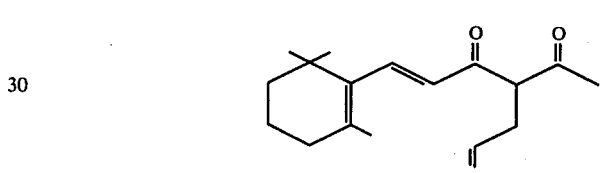

Figure 4:
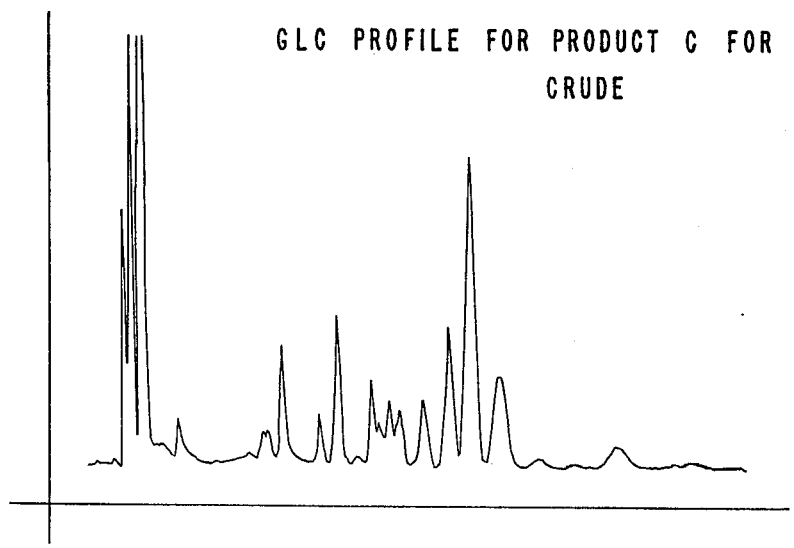

FIG. 4 is the GLC profile for the crude product produced according to Example I, product "C", containing the compounds defined according to the structure:

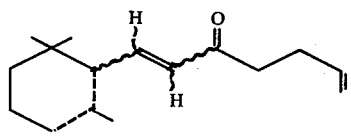

which defines a mixture wherein in the mixture, one of the dashed lines represents a carbon-carbon double bond and the other of the dashed lines represent carbon-carbon single bonds and the wavy lines represent cis and trans juxtaposition of the acyl and cyclohexenyl moieties about the carbon-carbon double bond alpha to the acyl moiety. (Conditions: 6'×0.25" 12% SF-96 column programmed from 80°-220° C. at 16° C. per minute.)

Figure 5:
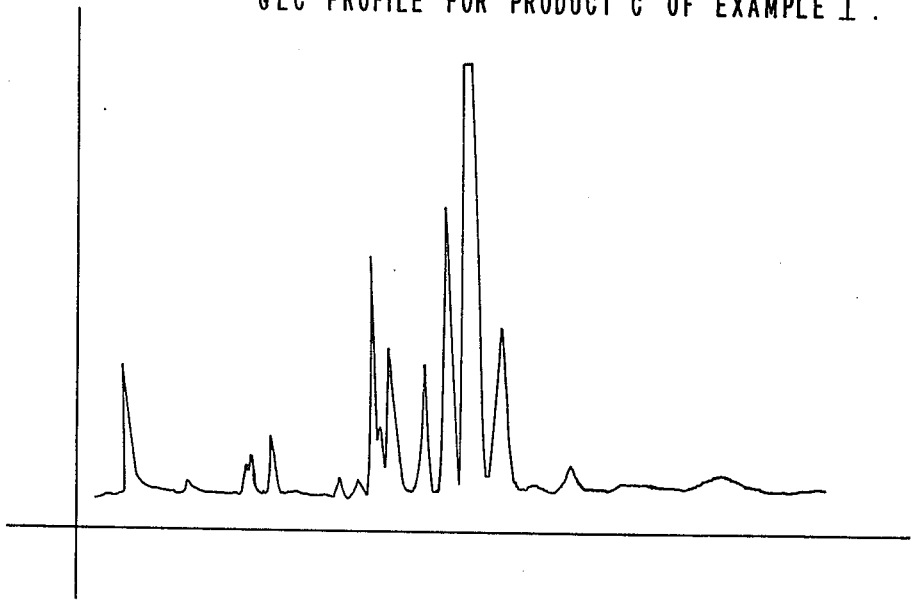

FIG. 5 is the GLC profile for product "C" after work-up but prior to distillation, produced according to Example I, said product "C" being a mixture of compounds defined according to the structure:

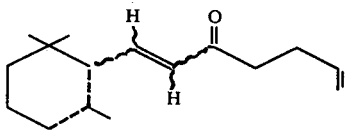

wherein the wavy lines and dashed lines are defined supra.

Figure 6:
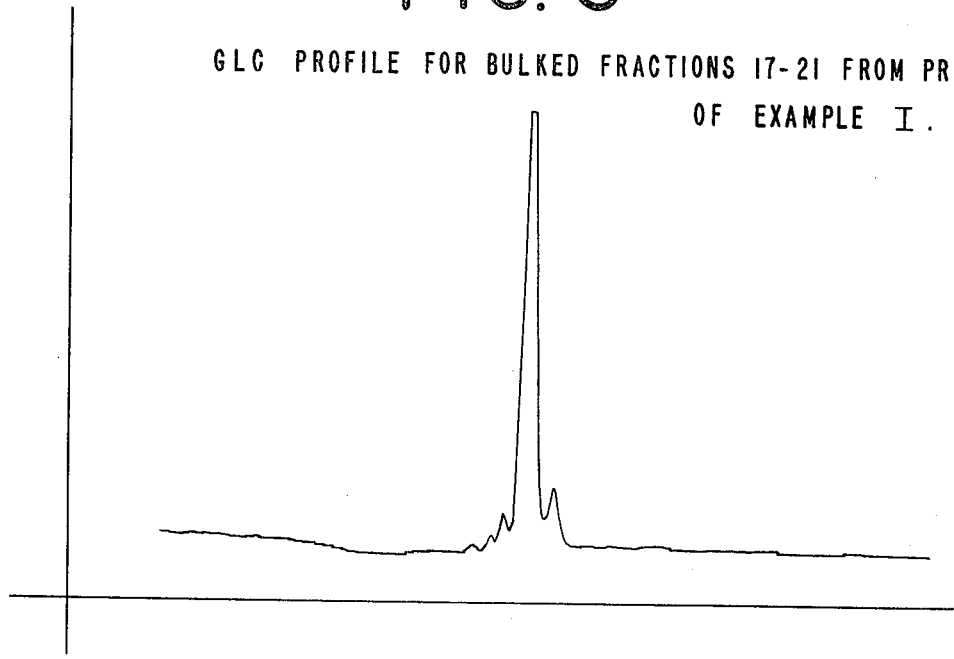

FIG. 6 is the GLC profile for bulked fractions 17-21 of the distillation product of the reaction product of Example I consisting of product "C" which is a mixture of compounds defined according to the structure:

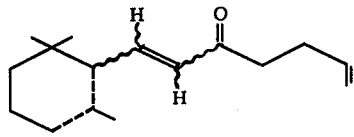

wherein the dashed lines and the wavy lines are defined supra.

THE INVENTION

Our invention relates to a process for preparing the compounds defined according to the generic structure:

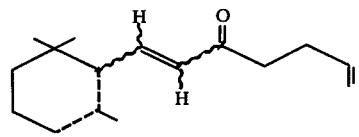

wherein one of the dashed lines represents a carbon-carbon double bond and the other of the dashed lines represents a carbon-carbon single bond and wherein the wavy lines represent the cis and trans juxtaposition of the cyclohexenyl and acyl moieties about the carbon-carbon double bond alpha to the acyl moiety, comprising the steps of reacting at least one compound defined according to the generic structure:

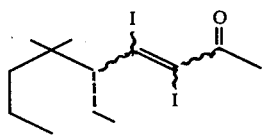

with at least one compound defined according to the generic structure:

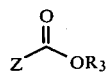

wherein Z represents methyl or $OR_2$ and wherein $R_2$ represents methyl or ethyl, and where $R_3$ represents $C_1-C_4$ alkyl in order to form at least one compound defined according to the generic structure:

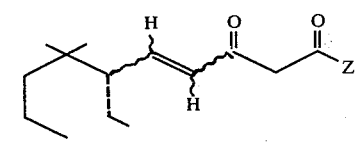

The compound defined according to the generic structure:

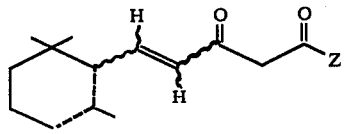

is then reacted with an allylic halide defined according to the structure:

wherein X is chloro, bromo or iodo with the proviso that when Z is methyl, then X represents bromo or iodo, in order to produce at least one compound defined according to the structure:

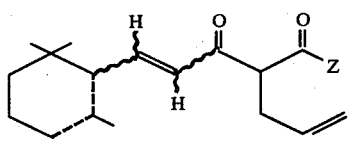

Depending on whether Z is $OR_2$ or methyl, the next sequence of reactions is either a retro-Claisen reaction or a decarboxylation reaction. Thus, according to one embodiment of our process, at least one compound having the structure:

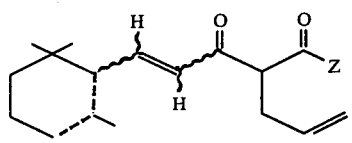

is reacted with an alkali metal alkoxide by means of a retro-Claisen reaction whereby at least one compound having the structure:

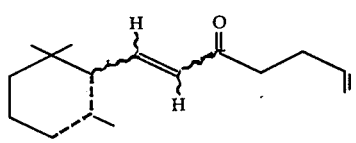

is formed directly. In a second embodiment of our invention, the compound having the structure:

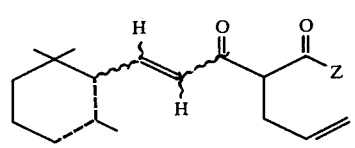

wherein Z is $OR_2$, is hydrolyzed using base in order to form at least one of the compounds defined according to the structure:

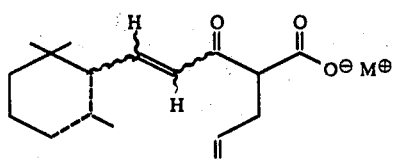

wherein M represents alkali metal such as sodium, potassium and lithium. The compound having the structure:

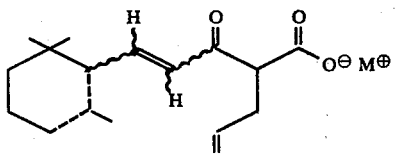

is then acidified to form at least one carboxylic acid having the structure:

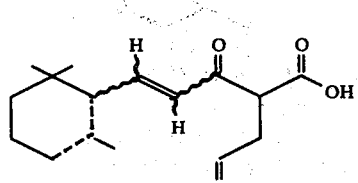

which, in turn, is then decarboxylated to form at least one of the compounds having the structure:

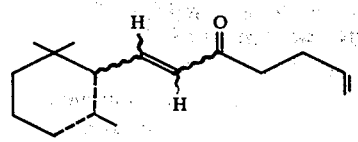

Thus, our process is embodied in the following generic reaction scheme:

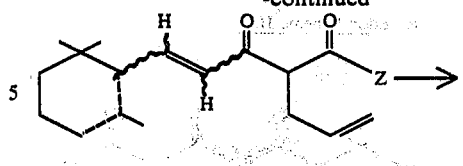

As stated supra, the last reaction (iii) may be a onestep retro-Claisen where Z is methyl or it may be carried out in several steps if Z is $OR_2$. Accordingly, our process may be specifically shown using two alternative sequences:

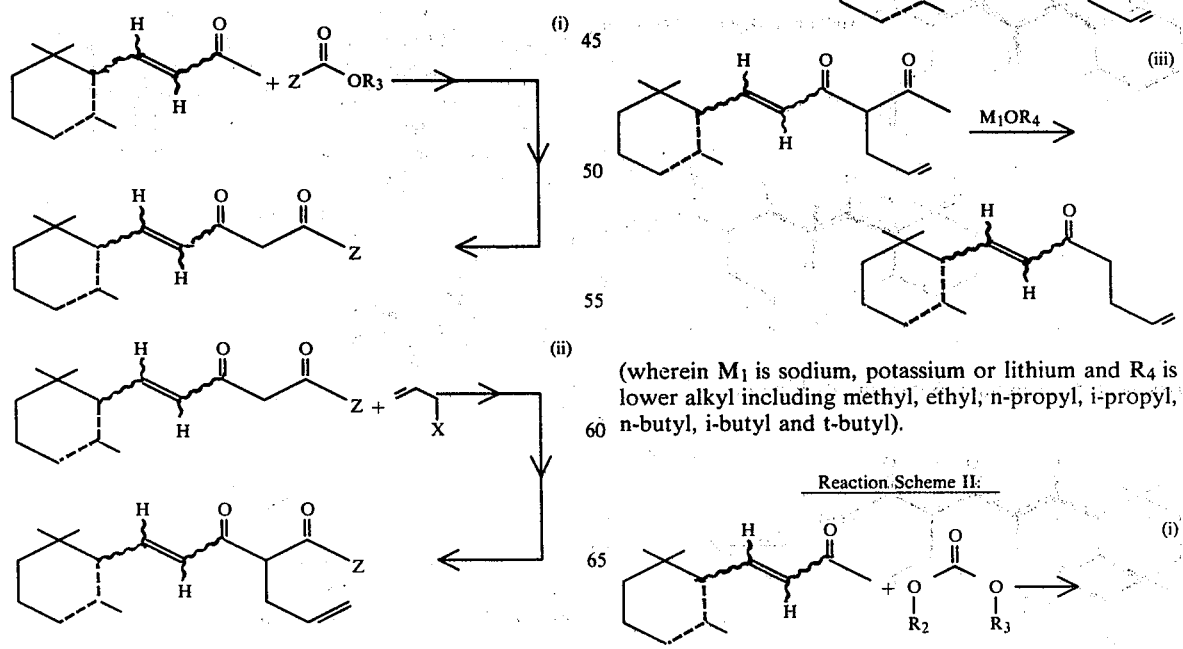

(wherein $M_1$ is sodium, potassium or lithium and $R_4$ is lower alkyl including methyl, ethyl, n-propyl, i-propyl, n-butyl, i-butyl and t-butyl).

-continued
Reaction Scheme II:

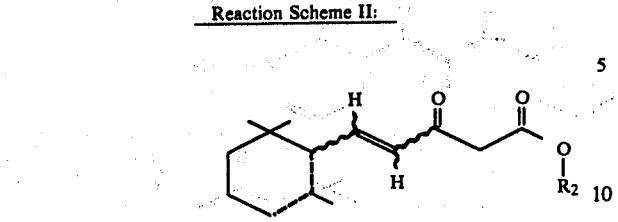

(ii)

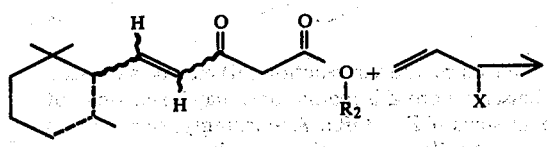

(iii)

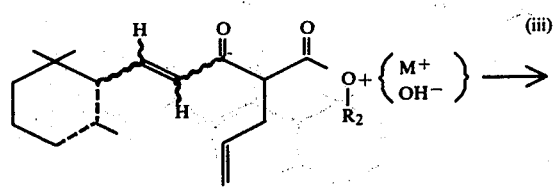

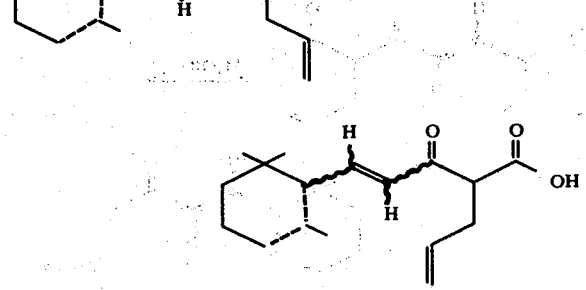

(iv)

(wherein M is sodium, potassium or lithium)

(v)

-continued

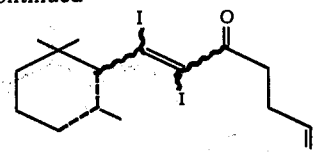

Referring to reaction sequence I and referring to the first reaction therein, to wit:

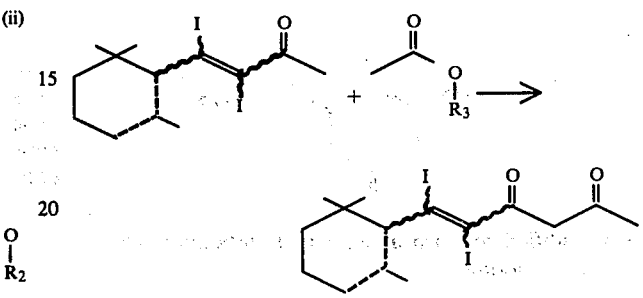

$R_3$ may be $C_1$–$C_5$ lower alkyl including methyl, ethyl, 1-propyl, 2-propyl, 1-butyl, 2-butyl, 1-methyl-2-propyl, and 2-methyl-2-propyl. The reaction takes place at a temperature in the range of from about 20° C. up to about 50° C. and a pressure in the range of from about 0.7 atmospheres up to about 5 atmospheres, preferably at a temperature of from about 30 up to about 40° C. and at 1 atmosphere pressure. The reaction takes place using an alkali metal alkoxide catalyst such as sodium methoxide, sodium isopropoxide, potassium methoxide, potassium isopropoxide and aluminum triisopropylate. The mole ratio of ionone derivative having the structure:

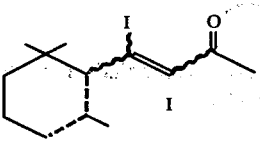

to alkyl acetate is between 1:1 and 1:2 with a preferred mole ratio of ionone compound:alkyl acetate of about 1:1.5. The mole ratio of alkali metal alkoxide:alpha ionone is between 0.5:1 and 1:0.5 with a preferred mole ratio of alkali metal alkoxide:ionone compound being about 1:1.

In carrying out the reaction (ii) of this sequence I, to wit:

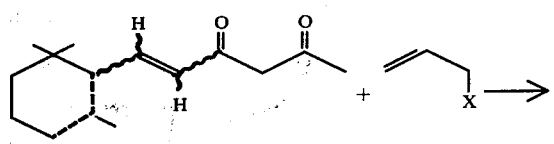

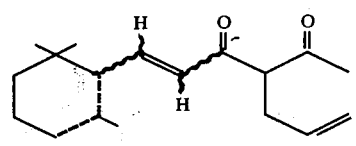

the mole ratio of compound having the structure:

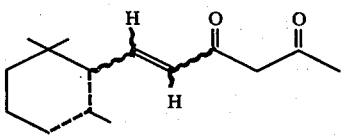

to the allyl halide having the structure:

is between 1:1 and 1:2 with a preferred mole ration of about 1:1. In this reaction, the allyl halide having the structure:

is one wherein X is bromo or iodo. Actually, allyl chloride can be used as a reactant but the allyl iodide or allyl bromide must be produced in situ. Accordingly, conveniently, allyl chloride may be used along with such a material as sodium iodide or sodium bromide whereby the allyl iodide or allyl bromide is produced in situ.

This reaction takes place at reflux conditions, preferably at a temperature in the range of from about 60 up to about 80° C., most conveniently at atmospheric pressure. However, pressures greater than or less than atmospheric pressure may be used. Accordingly, the pressure of reaction may vary from about 0.7 atmospheres up to about 10 atmospheres at reflux conditions. Higher temperatures of reaction give rise to shorter time periods of reaction. For example, when carrying out the reaction at 60°–70° C., the time of reaction is about 8 hours.

At the end of this reaction, the reaction mass is purified by means of solvent stripping. The reaction product is then further reacted by means of reaction (iii), to wit:

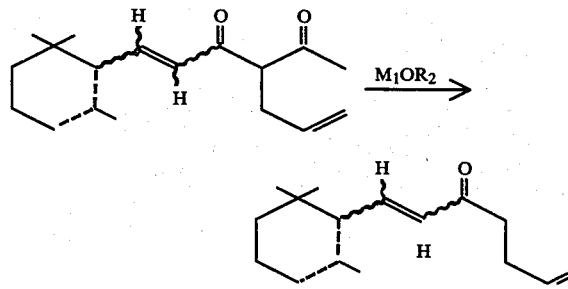

wherein $M_1$ is alkali metal such as sodium, potassium and lithium and $R_4$ is lower alkyl such as methyl, ethyl, 1-propyl, 2-propyl, 1-methyl-2-propyl and 2-methyl-2-propyl. The reaction preferably takes place in aqueous solution. In place of the alkali metal alkoxide used, an aqueous alcoholic alkali metal hydroxide solution can be used. Thus, for example, one liter of 50% aqueous sodium hydroxide may be admixed with 500 ml water and 500 ml methyl alcohol and the resulting mixture is then admixed with the compound having the structure:

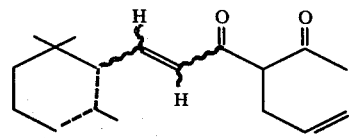

This reaction is carried out at a temperature of between 35° and 50° C.

The resulting product is then distilled from the reaction mass by means of fractional distillation at a vapor temperature of 108°–128° C. and a pressure of 3.0 mm/Hg.

Referring now to reaction sequence II, in carrying out the reaction (i), to wit:

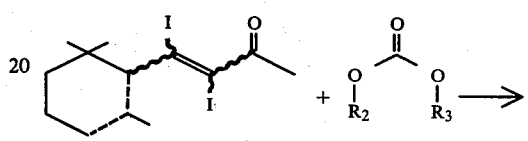

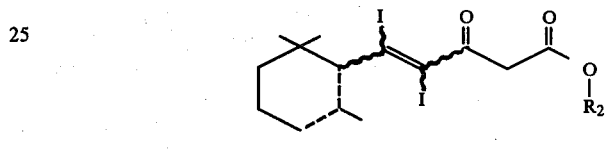

the dialkyl carbonate defined according to the structure:

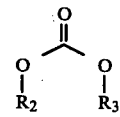

can be used as the solvent so that excess dialkyl carbonate is preferably used. The reaction is carried out using as an additional reagent, an alkali metal hydride such as sodium hydride, potassium hydride or an alkaline earth metal hydride catalyst such as calcium hydride or magnesium hydride. The reaction temperature may vary from 25° C. up to 100° C. but the reaction is preferably carried out at reflux conditions. The mole ratio of ionone derivative having the structure:

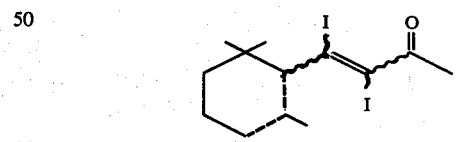

to alkali metal hydride or alkaline earth metal hydride: dialkyl carbonate may vary from about 1:2:1 up to about 1:2:2.

In carrying out the reaction of the thus-formed diketo ester defined according to the structure:

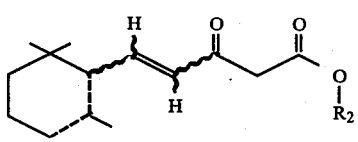

with the allyl halide having the structure:

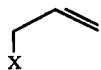

wherein X is chloro, bromo or iodo, this reaction is carried out in the presence of an alkali metal alkoxide such as sodium ethoxide, sodium methoxide, potassium methoxide, potassium ethoxide or potassium t-butoxide or an alkali metal hydride such as sodium hydride, potassium hydride or lithium hydride or an alkaline earth metal hydride such as calcium hydride or magnesium hydride in order to form the substituted ketoester defined according to the structure:

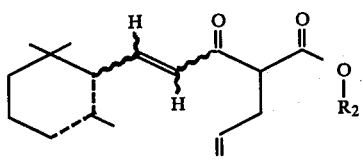

The mole ratio of ketoester having the structure:

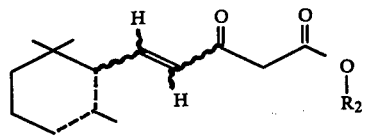

to allyl halide:alkali metal alkoxide or alkali metal hydride or alkaline earth metal hydride is preferably 1:1:1. This particular reaction preferably takes place in the presence of an inert solvent which will not react with the other reactant such as toluene, benzene or xylene.

The saponification of the substituted ketoester to form the substituted ketocarboxylic acid alkali metal salt defined according to the structure:

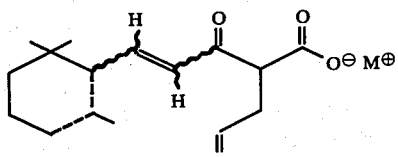

wherein M is alkali metal such as lithium, sodium or potassium is carried out in the presence of a base such as sodium hydroxide, potassium hydroxide or lithium hydroxide in aqueous media according to standard saponification conditions. The resulting saponified material is then hydrolyzed in the presence of acid under standard hydrolysis conditions known in the art using such mineral acids as sulfuric acid, or hydrochloric acid in order to form the substituted carboxylic acid defined according to the structure:

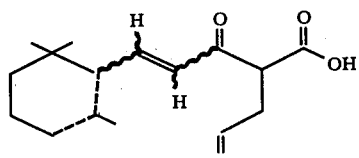

This material is then decarboxylated according to standard decarboxylation conditions in order to form at least one of the compounds having the structure:

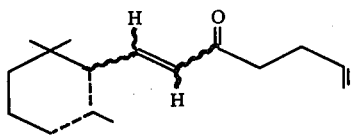

The following Examples I and II serve to illustrate methods for carrying out the processes of our invention and producing intermediates useful in our invention. All parts and percentages given herein are by weight unless otherwise specified.

EXAMPLE I

Reactions:

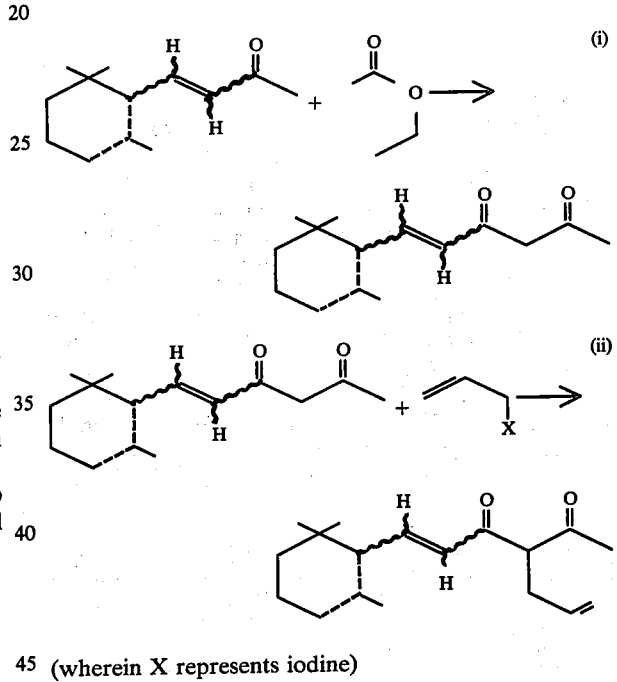

(wherein X represents iodine)

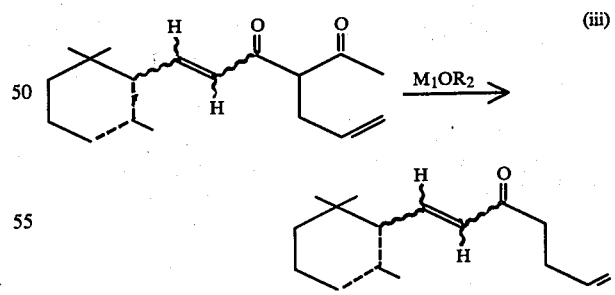

(wherein $M_1$ is sodium and $R_4$ is methyl)

Into a twelve liter reaction flask equipped with stirrer, condenser, "Y" tube, thermometer, additional funnel and gas bubbler is placed 2,940 ml of ethyl acetate (15 moles) and 540 grams of sodium methoxide (10 moles). The resulting solution is heated to 32° C. and over a period of two hours while maintaining the reaction mass at 32°–42° C., 1,152 grams (10 moles) of alpha ionone (a mixture of alpha ionone and beta ionone, 85:15) is added to the reaction mass from the addition funnel.

The resulting compound having the structure:

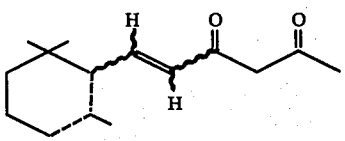

is then reacted in situ with allyl iodide formed in situ thusly:

To the reaction mass 150 grams (1 mole) of sodium iodide is added, with stirring while maintaining the temperature at 30° C. Over a period of 25 minutes, 600 ml (10 moles) of allyl chloride is added to the reaction mass while maintaining the reaction temperature at 30°–40° C. The reaction mass is then refluxed at 60°–70° C. for a period of 8 hours with stirring.

At the end of the reaction, 1.5 liters of water is added and the resulting mixture is stirred. The resulting mixture is transferred to a separatory funnel and the aqueous phase is separated from the organic phase. The organic phase is transferred to a 5 liter distillation flask and stripped of solvent to a pot temperature of 100° C. at 3.8 mm/Hg pressure.

The resulting product is fractionally distilled yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 32 | 37 | 100 | 350.5 |
| 2 | 34 | 40 | 20 | 397.4 |
| 3 | 35 | 44 | 16 | 429.0 |
| 4 | 37 | 50 | 16 | 408.0 |
| 5 | 38 | 78 | 16/7 | 238.7 |
| 6 | 50 | 100 | 3.8 | 37.4 |

Figure 1:
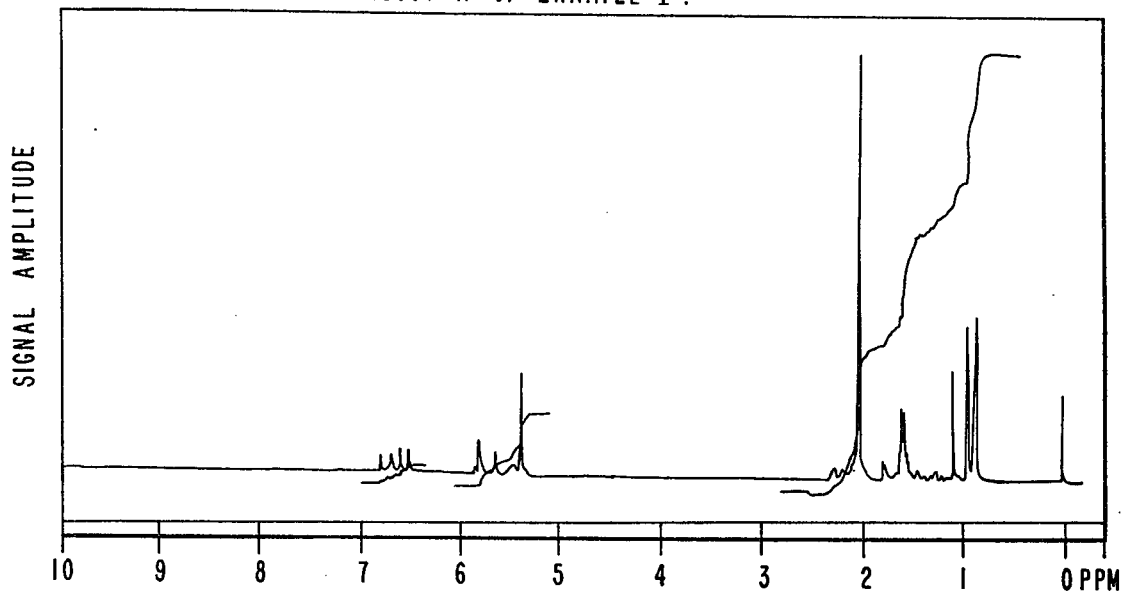
FIG. 1 is the NMR spectrum for product "A" of Example I which is a mixture of approximately 85% of the isomer having the structure.

FIG. 1 is the NMR spectrum for product "A" containing 85% by weight of the isomer:

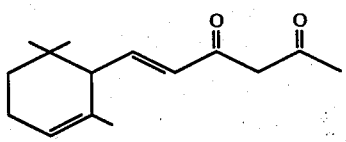

and 15% by weight of the isomer having the structure:

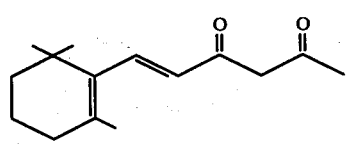

FIG. 2 is the NMR spectrum for product "B" which is a mixture of compounds having the structure:

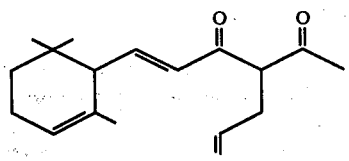

(85% by weight) and the structure:

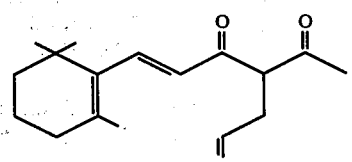

(15% by weight). Conditions for NMR: $CFCl_3$ solvent and 100 MHz field strength.

FIG. 3 is the infra-red spectrum for the mixture of compounds having the structures:

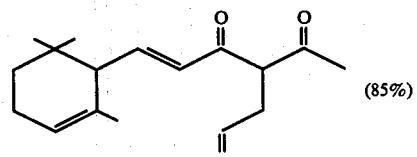 (85%)

and

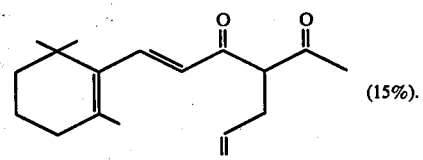 (15%).

The NMR assignments for the mixture of compounds having the structures:

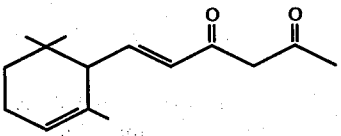

and

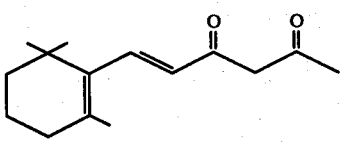

are as follows:

| | |
|---|---|
| δ0.87 | S 3H |
| δ0.92 | S 3H |
| δ1.08 | S 1H |
| δ1.5–1.6 | M 3H |
| δ2.03 | S 3H |
| δ5.37 | S 1H |
| δ5.4–55 | bM 1H |
| δ5.62–5.82 | M 1H |
| δ6.5–6.77 | M 1H |

The resulting reaction mass is then transferred back to the 12 liter reaction flask and a solution of:

1 liter 50% sodium hydroxide
500 ml methyl alcohol
500 ml water
previously heated to 55° C. is added to the flask while stirring. The resulting mixture is stirred for a period of 1.25 hours at 46° C.

The contents are transferred to a separatory funnel and the aqueous layer is separated from the organic layer. The organic phase is acidified to a pH of 6 by means of addition of 25 ml Glacial Acetic Acid. Sodium acetate salts form immediately. The organic material is then filtered through a Buchner funnel to remove the solids under a nitrogen blanket.

The resulting organic liquid is then distilled on a 12" Goodloe column yielding the following fractions:

| Fraction Number | Vapor Temp. (°C.) | Liquid Temp. (°C.) | Pressure mm/Hg | Reflux Ratio | Weight of Fraction (grams) |
| --- | --- | --- | --- | --- | --- |
| 1 | 43/39 | 107/120 | 4.4/3.0 | 9:1 | 10.0 |
| 2 | 83 | 125 | 3.0 | 9:1 | 25.8 |
| 3 | 95 | 128 | 3.0 | 9:1 | 39.3 |
| 4 | 95 | 128 | 3.0 | 9:1 | 13.5 |
| 5 | 95 | 132 | 3.0 | 9:1 | 16.0 |
| 6 | 97 | 132 | 3.0 | 9:1 | 20.7 |
| 7 | 99 | 134 | 2.8 | 9:1 | 20.0 |
| 8 | 103 | 135 | 3.0 | 9:1 | 15.6 |
| 9 | 107 | 135 | 3.0 | 9:1 | 19.2 |
| 10 | 108 | 136 | 3.0 | 9:1 | 24.8 |
| 11 | 109 | 139 | 3.0 | 9:1 | 34.7 |
| 12 | 112 | 140 | 3.0 | 9:1 | 43.4 |
| 13 | 113 | 141 | 3.0 | 9:1 | 27.6 |
| 14 | 117 | 141 | 3.0 | 9:1 | 27.2 |
| 15 | 120 | 142 | 3.0 | 9:1 | 29.7 |
| 16 | 122 | 145 | 3.0 | 9:1 | 30.3 |
| 17 | 124 | 147 | 3.0 | 4:1 | 52.1 |
| 18 | 125 | 148 | 3.0 | 4:1 | 48.4 |
| 19 | 126 | 150 | 3.0 | 4:1 | 46.3 |
| 20 | 128 | 153 | 3.0 | 4:1 | 53.5 |
| 21 | 128 | 154 | 3.0 | 4:1 | 41.0 |
| 22 | 123 | 155 | 3.0 | 4:1 | 39.8 |
| 23 | 125 | 163 | 3.0 | 1:1 | 55.9 |
| 24 | 128 | 196 | 3.0 | | 86.2 |
| 25 | 123 | 215 | 3.0 | | 16.2 |
| 26 | 126 | 240 | 2.5-3.0 | | 33.1 |

Fractions 2-9 represent recovered alpha ionone.

Fractions 10-25 represent the allyl ionone mixture defined according to the structure:

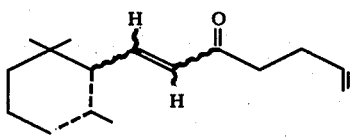

with a preponderance of the compound having the structure:

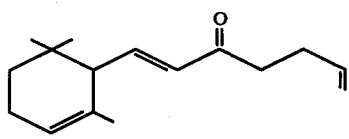

being present.

FIG. 4 is the GLC profile for crude reaction product "C" defined according to the structure:

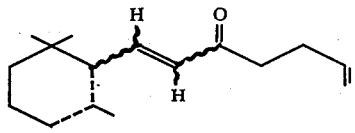

(Conditions: 6'×0.25" 12% SF-96 column programmed at 80°-220° C. at 16° C. per minute.)

FIG. 5 is the GLC profile of the acidified reaction product "C" defined according to the structure:

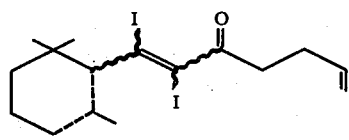

(Conditions: 6'×0.25" 12% SF-96 column programmed at 80°-220° C. at 16° C. per minute.)

FIG. 6 is the GLC profile for bulked fractions 17-21 of product "C" having the structure:

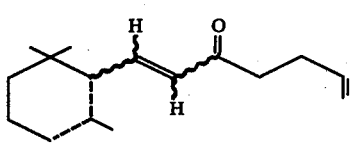

EXAMPLE II

Reactions:

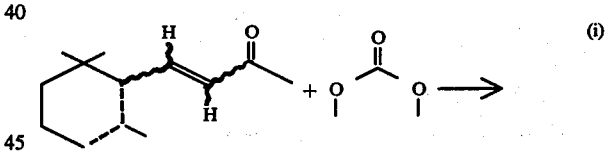 (i)

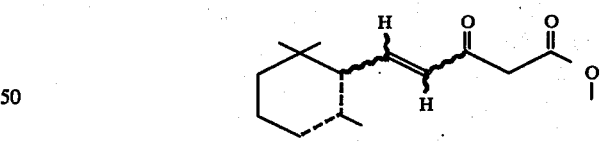

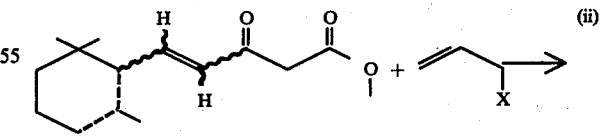 (ii)

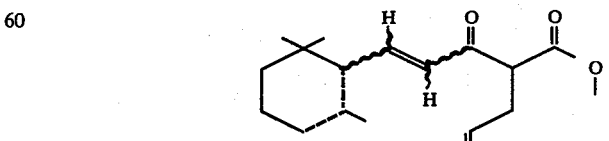

(wherein X is chloro)

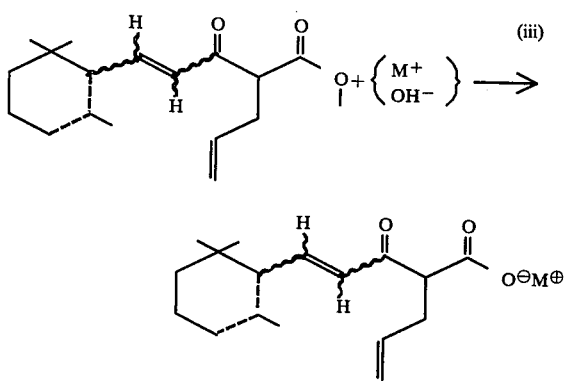

(wherein M is sodium)

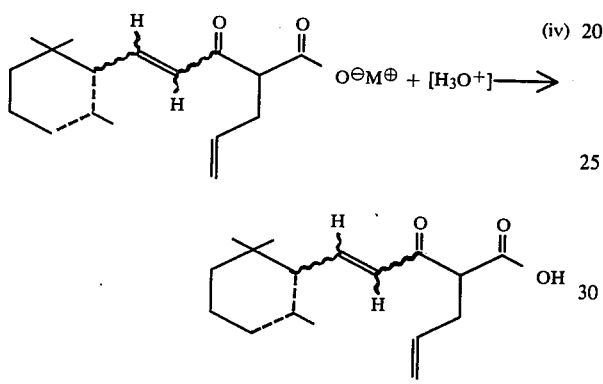

(wherein M is sodium)

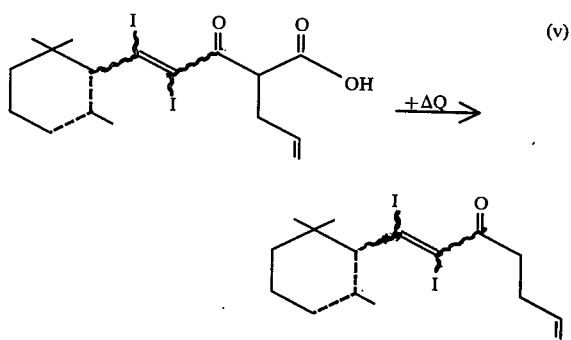

Into a ten liter reaction vessel equipped with stirrer, thermometer and reflux condenser is placed 504 grams of 50% sodium hydride and five liters of toluene. The resulting mixture is heated to 50° C. and 540 grams (6 moles) of dimethyl carbonate is slowly added. The reaction mass is heated to 80° C. and while maintaining the reaction mass at 80° C., five moles of alpha ionone is added to the reaction mass. Twelve ml of methanol is then added to the reaction mass and the reaction mass is then stirred for a period of 13 hours at 80° C.

Over a period of 0.5 hours, while maintaining the reaction mass at 70° C., 420.7 grams (5.5 moles) of allyl chloride is added to the reaction mass. The reaction mass is then stirred at 70° C. for a period of 8 hours.

The reaction mass is then admixed with 760 grams (12 moles) of sodium hydroxide and 1000 grams of water and refluxed with water for a period of 3 hours. The reaction mass is then slowly quenched with concentrated hydrochloric acid until the pH is 1. The reaction mass is then heated until no carbon dioxide is evolved. The reaction mass is washed as follows:

2 liters water
2 liters 10% sodium carbonate.

The reaction product is then distilled on an 18" Goodloe column at a vapor temperature of 122°–125° C.; a liquid temperature of 142°–149° C. and a vacuum of 3.0 mm/Hg pressure, thereby yielding a mixture of compounds defined according to the structure:

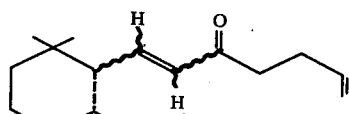

What is claimed is:
1. At least one compound defined according to the structure:

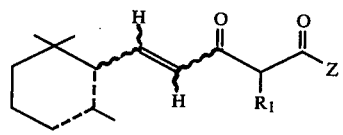

wherein $R_1$ represents hydrogen or 2-propenyl; wherein Z represents methyl or $OR_2'$; wherein $R_2'$ represents methyl, ethyl, hydrogen or alkali metal; wherein one of the dashed lines represents a carbon-carbon double bond and the other of the dashed lines represents a carbon-carbon single bond; and wherein the wavy lines represent the "cis" or "trans" juxtaposition of the cyclohexenyl and acyl moieties about the carbon-carbon double bond which is alpha to the acyl moiety with the proviso that Z is methyl when $R_1$ is hydrogen.

2. The compound of claim 1 wherein $R_1$ is allyl.
3. The compound of claim 1 wherein $R_1$ is hydrogen and Z is methyl.
4. The compound of claim 1 wherein Z is methyl.
5. The compound of claim 1 wherein $R_1$ is allyl and Z is methyl.
6. The compound of claim 1 wherein $R_1$ is allyl and Z is $OR_2$; and $R_2$ is methyl or ethyl.
7. The compound of claim 1 wherein $R_1$ is allyl and Z represents OH.
8. The compound of claim 1 wherein $R_1$ is allyl and Z represents $O^-M^+$; wherein M is alkali metal selected from the group consisting of sodium, potassium and lithium.

* * * * *